(12) United States Patent
Yamamoto et al.

(10) Patent No.: US 7,500,502 B2
(45) Date of Patent: Mar. 10, 2009

(54) INSPECTION APPARATUS AND METHOD FOR FILM CARRIER TAPES FOR MOUNTING ELECTRONIC COMPONENTS AND SEMICONDUCTOR DEVICES

(75) Inventors: Masahiko Yamamoto, Shimonoseki (JP); Yoshihiro Kouzan, Hida (JP); Sachio Noto, Hida (JP); Kiyohito Kobayashi, Hida (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 779 days.

(21) Appl. No.: 11/058,858

(22) Filed: Feb. 16, 2005

(65) Prior Publication Data
US 2005/0183521 A1  Aug. 25, 2005

(30) Foreign Application Priority Data
Feb. 19, 2004  (JP) .............................. 2004-043259

(51) Int. Cl.
*B32B 41/00* (2006.01)
(52) U.S. Cl. ..................................... 156/379; 359/804
(58) Field of Classification Search ................ 156/379; 359/804; 242/538.2
See application file for complete search history.

(56) References Cited

U.S. PATENT DOCUMENTS 1,803,411 A * 5/1931 Stechbart .................... 352/130
3,798,807 A * 3/1974 Stewart ....................... 40/471
4,650,314 A * 3/1987 Grunwald ................... 355/40
6,634,159 B1  10/2003 Muto et al.
7,219,708 B2 * 5/2007 Yamamoto et al. .......... 156/361

FOREIGN PATENT DOCUMENTS

| JP | 4244905 A | 9/1992 |
| JP | 5036757 A | 2/1993 |
| JP | 6166951 A | 6/1994 |
| JP | 2001-345345 A | 12/2001 |
| JP | 2003332392 A * | 11/2003 |
| KR | 20010050508 A | 6/2001 |
| KR | 200321062 | 7/2003 |

* cited by examiner

*Primary Examiner*—Sang Kim
(74) *Attorney, Agent, or Firm*—The Webb Law Firm

(57) ABSTRACT

An inspection apparatus and method of inspection enable an inspector to conduct visual inspection of film carrier tapes for mounting electronic components in a natural sitting position regardless of the magnification of a magnifier. The inspection apparatus is compact to permit effective use of the space inside the inspection room. The inspection apparatus includes a feed reel and a take-up reel adjacent to each other, and an inspection part that is located so that the adjacent feed and take-up reels are in the order of the feed reel and the take-up reel in relation to the inspection part. A film carrier tape from the feed reel is transported in a substantially vertical direction to the inspection part and is inspected with a magnifier along a substantially vertical direction.

17 Claims, 8 Drawing Sheets

(A)

(B)

INSPECTION APPARATUS AND METHOD FOR FILM CARRIER TAPES FOR MOUNTING ELECTRONIC COMPONENTS AND SEMICONDUCTOR DEVICES

FIELD OF THE INVENTION

The present invention relates to an apparatus and a method for inspecting film carrier tapes for mounting electronic components (hereinafter, the "film carrier tapes") and semiconductor devices, wherein final inspection for defective leads and other defects is performed for the film carrier tapes before and after the mounting of semiconductors or other electronic components, and defective film carriers are marked as such by punching or the like. The inspection apparatus and method of the present invention may be suitably used for such film carrier tapes as TAB (tape automated bonding) tapes, COF (chip on film) tapes, T-BGA (tape ball grid array) tapes, CSP (chip size package) tapes, ASIC (application specific integrated circuit) tapes, and 2-metal (double-sided wiring) tapes.

BACKGROUND OF THE INVENTION

The demand for printed wiring boards for mounting electronic components such as IC (integrated circuits) tips and LSI (large-scale integrations) tips grows sharply with development of the electronics industry. With the required size and weight reduction and higher performance of electronic devices, film carrier tapes such as TAB tapes, COF tapes and T-BGA tapes are employed in the mounting of the electronic components. In particular, the film carrier tapes are of growing importance in the electronics industry where liquid crystal displays (LCD) such as personal computers are required for higher definition, thickness reduction and smaller frame area around the liquid crystal screen.

The film carrier tapes are generally quality inspected before and after electronic components such as semiconductors are mounted thereon. Specifically, appearance is visually checked by human eyes (a visual inspection using transmitted light or reflected light from the film carrier tape to be inspected) for defects in wiring patterns such as electrical disconnection, short-circuits, flaws and protrusions, defective plating, deformed tapes, imperfect solder resists and so on. Defective film carriers are marked using a defect marking device such as a punching device to form a hole mark or a stamping device to form an ink mark or using a magic marker.

Conventionally, inspection of the film carrier tapes has been carried out with an inspection apparatus as shown in FIG. 9 (see, for example, JP-A-2001-345345). The illustrated inspection apparatus 100 includes a feed device 102, an inspection part 110 and a take-up device 106.

The feed device 102 has a feed drive shaft 104 to which a feed reel 103 is attached. On the feed reel 103, a film carrier tape T for mounting electronic components (hereinafter, the film carrier tape T) is wound together with a spacer S. A drive motor (not shown) rotates the feed drive shaft 104 and thereby the film carrier tape T is fed together with the spacer S from the feed reel 103 and is transported to the inspection part 110 via a guide roller 115.

To inspect the film carrier tape T at the inspection part 110, a drive gear 122 that transports the film carrier tape T by engaging with sprocket holes of the tape T is temporarily stopped so that the film carrier tape T is exactly located at a predetermined inspection position. In the figure, the numeral 121 denotes a back tension device that applies back tension to the film carrier tape T being transported in a horizontal direction from upstream to downstream of the inspection part 110.

The inspection part 110 is equipped with a magnifier such as a microscope 111 for visual inspection using reflected or transmitted light for defects in wiring patterns such as electrical disconnection, short-circuits, flaws and protrusions, defective plating such as plating stain, deformation such as warpage of the tape, and imperfect solder resists such as scattered solder resists and pinholes. With the transportation of the film carrier tape T being suspended, one of wiring patterns arranged in line in a longer direction of the film carrier tape T is located at a predetermined inspection position and is visually inspected. When any defective parts are detected, they are marked as such by a defect marking device 112 by punching or ink marking.

After the visual inspection and the defect marking steps, the film carrier tape T is wound up on a take-up reel 107 attached to a take-up drive shaft 108 of a take-up device 106, via a guide roller 116. At the same time, the spacer S fed from the feed reel 103 via spacer guide rollers 117 and 118 is wound on the take-up reel 107. As a result, the film carrier tape T is wound around the take-up reel 107, with the spacer S interposing between the layers of tape wound on the take-up reel 107.

The numerals 125 and 126 denote dancer rollers that apply tension to the film carrier tape T being transported.

The wiring patterns on the film carrier tapes tend to be formed with finer pitches. When such fine-pitch patterns are visually inspected with the magnifier 111, the focal length of the lens needs to be shortened to ensure a required magnification for overall inspection of the wiring pattern. As shown in FIG. 8, the distance L from the eyepiece P1 to the inspection position P2 of the film carrier tape T is reduced.

When the distance L is reduced, that is, when the eyepiece P1 is lowered toward the floor on which the inspection apparatus 100 is placed, the inspector is caused to look through the eyepiece lenses in a forward leaning position rather than in a natural sitting position on a chair. For example, the film carrier tape and the lenses are about 21 cm apart when the magnification is 2.6×, but 4.1× magnification makes the distance between them 13 cm.

The visual inspection of the film carrier tape is performed with respect to wiring patterns that are arranged in a longer direction of the long tape wound on the feed reel 103. Therefore, the inspector has to maintain the forward leaning position over a long time. Further, microscopic foreign matters from the inspector will more likely fall on the inspected film carrier tape.

When a plurality of the film carrier tapes are inspected in parallel to each other at the inspection part across a large width of the tapes combined in the same field of view of the magnifier, the magnification is often lowered. In such cases, the focal length of the lenses is extended, and the distance L from the eyepiece P1 to the inspection position P2 of the film carrier tapes T increases as shown in FIG. 8. Because of this extended focal length, the inspector sitting on a chair of appropriate height is required to raise the seat height to conduct visual inspection through the eyepiece, which is unfavorable for safety reasons. In some cases, the eyepiece lenses can be raised so high that the inspector has to stand up to look through them. Because the visual inspection of the film carrier tape takes a long time as described above, such long inspection in a standing position causes undue fatigue to the inspector.

Furthermore, the visual inspection is generally carried out with a plurality of the inspection apparatuses 100 arranged in a room, so that it is preferred that each apparatus occupies a small space to effectively use the space inside the room.

The present invention has been made to solve the aforesaid problems of the prior art. It is therefore an object of the invention to provide an inspection apparatus and method for film carrier tapes for the mounting of electronic components and semiconductor devices whereby the inspector can conduct visual inspection of the film carrier tapes while sitting in a natural position on a chair of appropriate height regardless of the magnification of a magnifier, the inspection apparatus being compact to permit effective use of the space inside the inspection room.

SUMMARY OF THE INVENTION

An inspection apparatus for film carrier tapes for mounting electronic components according to the present invention comprises:

a feed device for feeding a film carrier tape wound on a feed reel;

an inspection part for inspecting the film carrier tape; and a take-up device for winding up the film carrier tape inspected at the inspection part on a take-up reel;

wherein the feed reel and the take-up reel are arranged adjacent to each other, and the inspection part is located so that the adjacent feed and take-up reels are in the order of the feed reel and the take-up reel or the take-up reel and the feed reel in relation to the inspection part.

This constitution achieves a more compact overall size of the inspection apparatus over the conventional apparatus constituted such that the inspection part is located between the feed reel and the take-up reel and the film carrier tape is transported across the inspection part in a horizontal direction.

With the conventional apparatus, the inspection part is located in a central area in the longer direction of the apparatus and the inspector faces the apparatus from the perpendicular direction to the longer direction of the apparatus. On the other hand, in the present invention, the inspector takes his position in front of the inspection part arranged at an end in the width direction of the apparatus, namely, the inspector faces the apparatus from the perpendicular direction to the width direction of the apparatus.

Accordingly, when two inspection apparatuses of the present invention are arranged with their back faces opposed to each other, both sides in the width direction of a pair of the inspection apparatuses can be used as passageways, permitting effective use of the space inside the inspection room.

The inspection apparatus of the invention is characterized in that it transports the film carrier tape in a substantially vertical direction at the inspection part so that the film carrier tape along the substantially vertical direction is inspected with a magnifier.

An inspection method for film carrier tapes for mounting electronic components according to the present invention comprises transporting a film carrier tape for mounting electronic components fed from a feed reel in a substantially vertical direction at an inspection part, and inspecting the film carrier tape along the substantially vertical direction with a magnifier.

According to this constitution, the magnifier of the inspection part is arranged in front of the surface of the film carrier tape that is transported in a substantially vertical direction. That is, the magnifier faces the tape surface along a horizontal direction. Accordingly, the focal length of lenses changes in a horizontal direction by magnification adjustment. Namely, the eyepiece does not move in a vertical direction in relation to the inspection position of the film carrier tape.

Therefore, the inspector can conduct visual inspection in a natural sitting position on a chair of appropriate height regardless of the magnification of the magnifier.

The inspection apparatus of the invention further comprises an upper guide roller and a lower guide roller above and below the inspection part respectively to transport the film carrier tape in a substantially vertical direction from the upper guide roller to the lower guide roller or from the lower guide roller to the upper guide roller.

The inspection method of the invention further comprises transporting the film carrier tape in a substantially vertical direction from an upper guide roller to a lower guide roller or from a lower guide roller to an upper guide roller, the upper guide roller and the lower guide roller being provided above and below the inspection part respectively.

The inspection apparatus of the invention is characterized in that the lower guide roller guides the film carrier tape such that the traveling direction of the tape is turned from the substantially vertical direction extending from the upper guide roller to the lower guide roller, to a substantially horizontal direction toward the side of the take-up reel, wherein the inspection apparatus further comprises a drive gear that is driven to transport the film carrier tape, the drive gear being provided at a position along the substantially horizontal direction, and tension devices at the upstream of the upper guide roller along the transportation direction and at the downstream of the drive gear along the transportation direction.

The inspection method of the invention further comprises:

guiding the film carrier tape by the lower guide roller such that the traveling direction of the tape is turned from the substantially vertical direction extending from the upper guide roller to the lower guide roller, to a substantially horizontal direction toward the side of the take-up reel;

transporting the film carrier tape by driving a drive gear provided at a position along the substantially horizontal direction; and applying tension by tension devices to the film carrier tape that is folded by the lower guide roller from the substantially vertical direction to the substantially horizontal direction, the tension devices being arranged at the upstream of the upper guide roller along the transportation direction and at the downstream of the drive gear along the transportation direction.

The inspection apparatus of the invention further comprises a defect marking device at a position along the substantially horizontal direction for marking a defect mark on the film carrier tape.

The inspection method of the invention further comprises marking a defect mark on the film carrier tape by a defect marking device provided at a position along the substantially horizontal direction.

The inspection apparatus of the invention is characterized in that a spacer is transported from the feed reel to the take-up reel directly not via a spacer guide roller.

The inspection method of the invention further comprises transporting a spacer from the feed reel directly to the take-up reel not via a spacer guide roller.

The inspection apparatus of the invention may comprise a plurality of pairs of the feed reel and the take-up reel adjacent to each other, wherein a plurality of the film carrier tapes fed from the respective feed reels are transported in parallel with each other in a substantially vertical direction at the inspection part and the film carrier tapes along the substantially vertical direction are inspected substantially simultaneously in the same field of view of the magnifier.

The inspection method of the invention may comprise:

feeding a plurality of the film carrier tapes from a plurality of the feed reels paired with a plurality of the take-up reels, the feed reels and the take-up reels being adjacent to each other;

transporting the film carrier tapes in parallel with each other in a substantially vertical direction to the inspection part; and inspecting substantially simultaneously the film carrier tapes parallel to each other along the substantially vertical direction in the same fields of view of the magnifier.

The inspection apparatus of the invention is characterized in that it allows an inspector to conduct visual inspection of the film carrier tape at the inspection part in which the film carrier tape is transported in a vertical direction across the field of view of the inspector.

The inspection method of the invention is characterized in that an inspector conducts visual inspection of the film carrier tape that is transported at the inspection part in a vertical direction across the field of view of the inspector.

An inspection apparatus and an inspection method for semiconductor devices according to the present invention are characterized in that semiconductor devices including a film carrier tape and electronic components mounted thereon are inspected instead of the film carrier tape for mounting electronic components.

The inspection method for semiconductor devices of the invention is characterized in that an inspector conducts visual inspection of the semiconductor devices that are transported at the inspection part in a vertical direction across the field of view of the inspector.

The inspection apparatus and method for film carrier tapes and semiconductor devices according to the present invention provide space-saving arrangement of the apparatuses by virtue of the compact apparatus size. Furthermore, the inspection apparatus and method enable the inspector to conduct visual inspection in a natural sitting position on a chair of appropriate height regardless of the magnification of the magnifier.

DETAILED DESCRIPTION OF THE INVENTION

Figure 1:
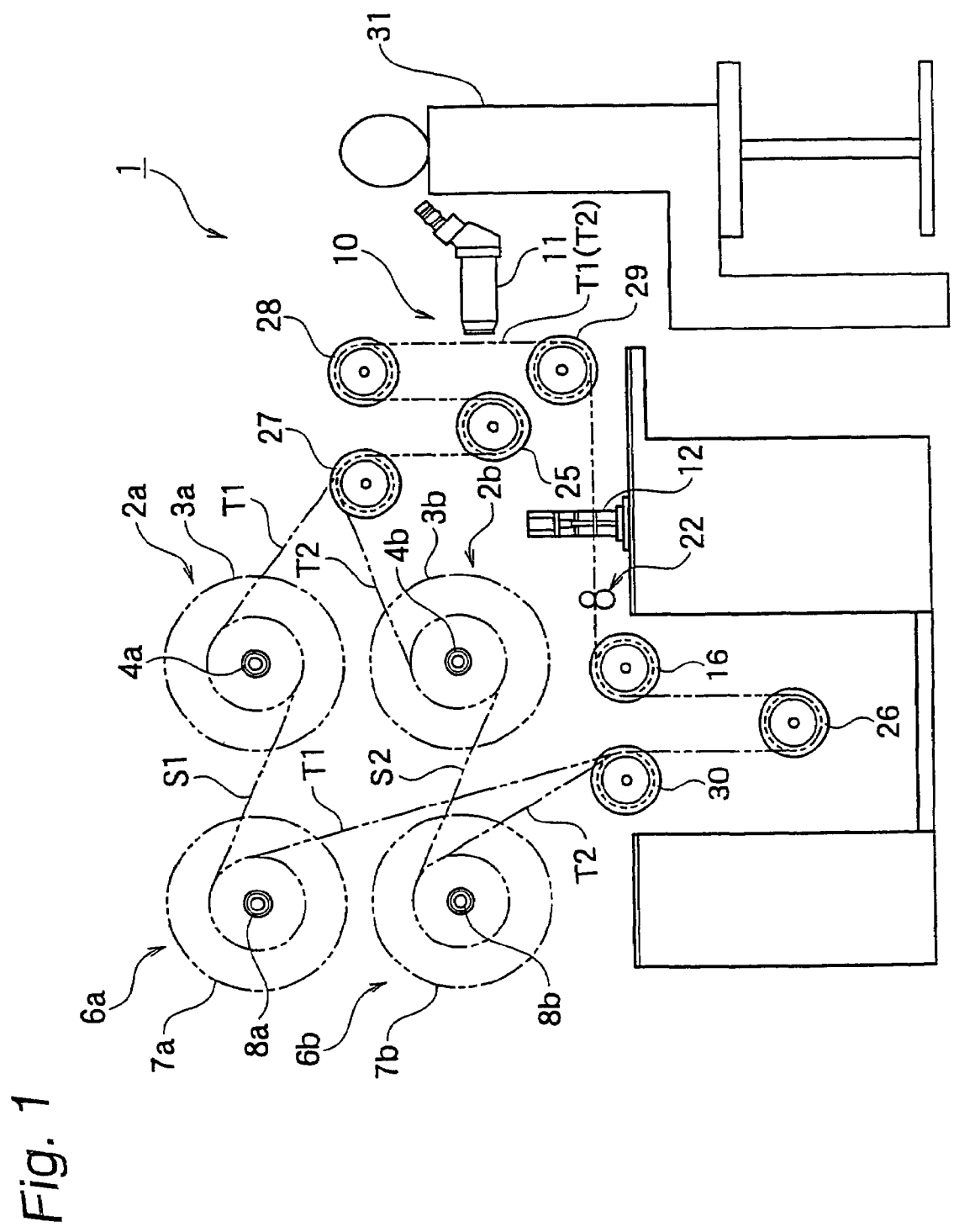
FIG. 1 is a front view illustrating the inspection apparatus for film carrier tapes according to an embodiment of the invention.

Hereinbelow, embodiments of the present invention will be described in detail with reference to the drawings. FIG. 1 is a front view illustrating the inspection apparatus for film carrier tapes according to an embodiment of the invention.

Figure 5:
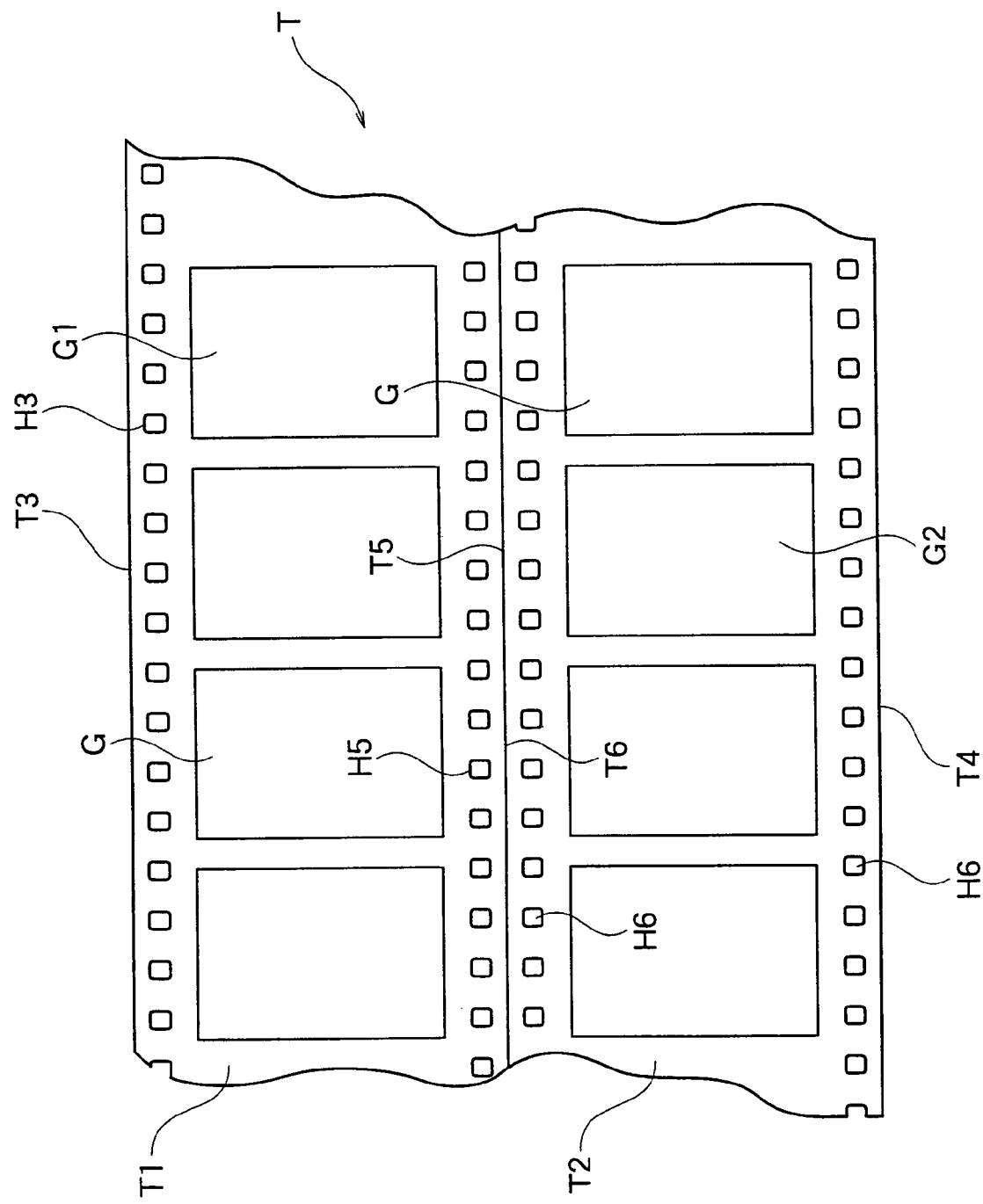
FIG. 5 is a top view showing a film carrier tape provided with two lines of wiring patterns.

An inspection apparatus 1 for film carrier tapes illustrated in FIG. 1 (hereinafter, the inspection apparatus 1) is constituted to simultaneously inspect two film carrier tapes T1 and T2 for mounting electronic components (hereinafter, the film carrier tapes T1 and T2). The inspection apparatus is provided with feed devices 2a and 2b that feed the respective film carrier tapes T1 and T2, an inspection part 10, and take-up devices 6a and 6b that wind up the respective inspected film carrier tapes T1 and T2. The film carrier tapes T1 and T2 may be those obtained by, for example, cutting with a slitter a film carrier tape (so-called multiple-carrier tape) that is provided with a plurality of wiring pattern units including a part on which an electronic component will be mounted (Such a wiring pattern unit may be called "piece" hereinafter.), the pieces G being aligned in two lines (pieces G1 and G2) in the width direction of the tape as shown in FIG. 5. In the invention, the tapes having a width of 35 mm, 48 mm, 70 mm or 96 mm each may be employed.

The feed device 2a has a feed drive shaft 4a fitted with a feed reel 3a. On the feed reel 3a, the film carrier tape T1 to be inspected is wound together with a spacer S1. Meanwhile, the take-up device 6a has a take-up drive shaft 8a fitted with a take-up reel 7a. The take-up reel 7a winds up the film carrier tape T1 that has been inspected, with the spacer S1 interposing between the layers of tape wound on the take-up reel. The feed reel 3a and the take-up reel 7a are arranged adjacent to each other in a substantially horizontal direction along the reel diameter. The spacer S1 is directly transported between these reels not via a spacer guide roller. The reels 3a and 7a may be arranged at an angle with respect to a depth direction of the apparatus in relation to an inspector 31. For example, they may be arranged such that the angle is 45°. It is also possible that the spacer S1 is transported via a spacer guide roller.

The feed device 2b has a feed drive shaft 4b fitted with a feed reel 3b. On the feed reel 3b, the film carrier tape T2 to be inspected is wound together with a spacer S2. Meanwhile, the take-up device 6b has a take-up drive shaft 8b fitted with a take-up reel 7b. The take-up reel 7b winds up the film carrier tape T2 that has been inspected, with the spacer S2 interposing between the layers of tape wound on the take-up reel. The feed reel 3b and the take-up reel 7b are likewise arranged adjacent to each other in a substantially horizontal direction along the reel diameter. The spacer S2 is directly transported between these reels not via a spacer guide roller. The reels 3b and 7b may be arranged at an angle with respect to a depth direction of the apparatus in relation to the inspector 31. For example, they may be arranged such that the angle is 45°. It is also possible that the spacer S2 is transported via a spacer guide roller. In FIG. 1, a pair of the adjacent feed reel 3a and take-up reel 7a and a pair of the adjacent feed reel 3b and take-up reel 7b are arranged one above the other with their widths aligned with each other. However, the alignment in the width direction may be altered appropriately depending on the layout of other devices.

The film carrier tapes T1 and T2 are fed together with the spacers S1 and S2 from the respective feed reels 3a and 3b by rotation of the feed drive shafts 4a and 4b by drive motors (not shown). The film carrier tapes T1 and T2 from the feed reels 3a and 3b are guided by a guide roller 27 and an upper guide roller 28 to a position on the side of the feed reels 3a and 3b, as illustrated. The film carrier tapes T1 and T2 are then introduced in parallel with each other to the inspection part 10. The position relationship among the feed reels, the take-up reels and the inspection part is in the order of the inspection part, the feed reels and the take-up reels. The numeral 25 is a tension device which applies tension to the film carrier tapes T1 and T2, and is a dancer roller in the present embodiment.

The film carrier tapes T1 and T2 have a substantially vertical direction from the upstream to the downstream of the inspection part 10. Herein, the substantially vertical direction is a gravitational direction or the opposite direction that is preferably inclined within 45°, more preferably within 20°, and optimally within 10° from the vertical line. That is, the upper guide roller 28 and a lower guide roller 29 are arranged such that the film carrier tapes T1 and T2 are transported in the substantially vertical direction. This substantially vertical transportation permits the inspector 31 to perform visual inspection of the film carrier tapes T1 and T2 through a low-power microscope 11 (magnifier) while he is seated facing nearly forward.

Through the microscope 11 (magnifier), the inspector 31 visually makes quality inspection for defects in wiring patterns such as electrical disconnection, short-circuits, flaws and protrusions by means of transmitted light or reflected light. Besides the microscopes, one-lens simple magnifiers such as a glass lens and a Fresnel lens are employable as the magnifier. Low-power microscopes are more desirable due to relatively easy installation. For example, the microscope 11 is arranged sideways to bring the optical system fitted with the lenses in a substantially horizontal direction so that the optical axis will be approximately perpendicular to the tape surface.

The magnification of the magnifier (with respect to onedimensional direction) is desirably in the range of 1.4 to 6.0×, preferably 1.8 to 5.5×, and more preferably 2.0 to 5.0×. The magnification less than 1.4× is so low that detection of defects is difficult. When the magnification exceeds 6.0×, the patterns may extend off the field of view.

Specifically, 2.0 to 6.0× magnification is preferable for a stereoscopic microscope having plural lenses, and 1.4 to 2.5× magnification is desirable for a one-lens simple magnifier. Where close inspection is required for a possibly defective pattern, the magnification may be increased to about 20×.

As an example, the film carrier tapes can be inspected with the magnifier as described below. The magnification is adjusted in the range of 2.0 to 6.0× so that a plurality of patterns will be in the field of view at a time. Although in principle the magnification will not be changed during the inspection, it may be increased when a possibly defective pattern requires close inspection. For example, when a possibly defective pattern is found through the stereoscopic microscope at a low magnification of 2.0 to 6.0×, the magnification may be increased to about 20×. When a possibly defective pattern is found with the magnifying glass, the magnifying glass may be replaced with a high-power stereoscopic microscope and the pattern in question may be closely inspected at about 20× magnification.

In the present embodiment, the film carrier tapes T1 and T2 parallel to each other are inspected at the inspection part 10 with the magnifier in a manner such that the two tapes T1 and T2 are inspected simultaneously across the width thereof. When a plurality of the film carrier tapes are inspected in the same field of view as in this embodiment, the width of the film carrier tapes combined is desirably 160 mm or less, preferably 130 mm or less, and more preferably 110 mm or less. It is required that a plurality of the patterns should be in the same field of view when inspected at the inspection part. That is, the film carrier tapes may not be aligned precisely as long as their relative positions are in the same field of view.

Figure 7:
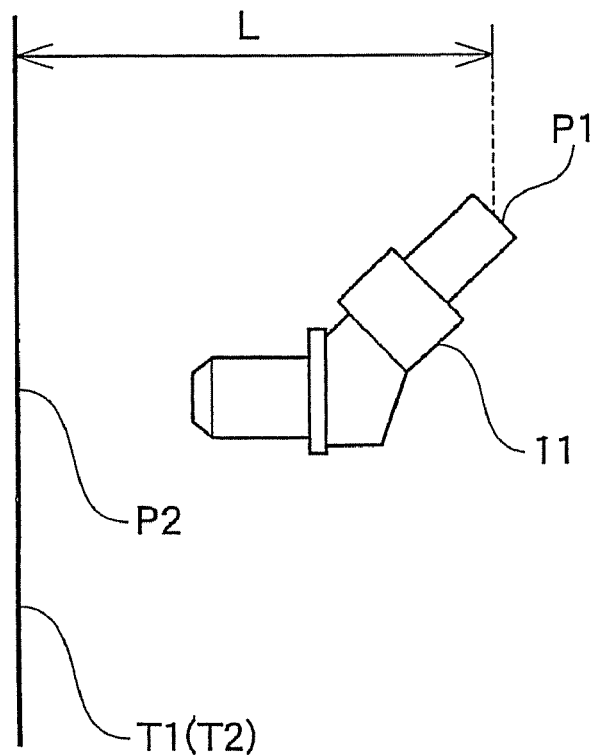
FIG. 7 is a view explaining the movement of a magnifier in the direction of focal length of the inspection apparatus of the present invention.
Figure 8:
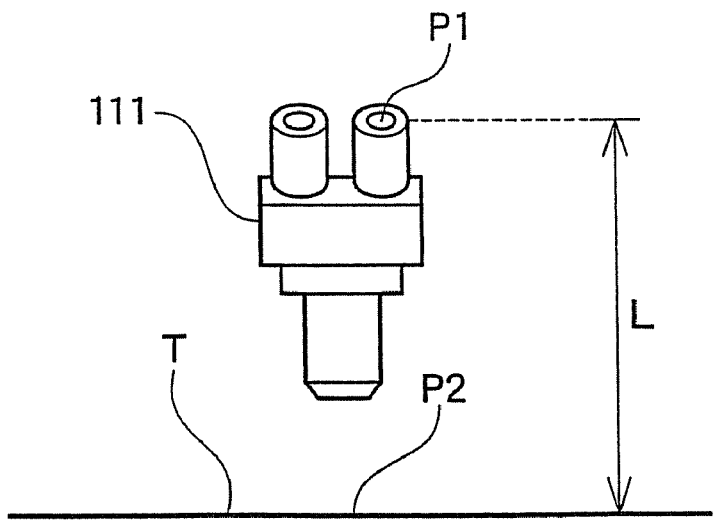
FIG. 8 a view explaining the movement of a magnifier in the direction of focal length of the conventional inspection apparatus.

As a result that the film carrier tapes T1 and T2 have a substantially vertical direction at the inspection part 10 and the microscope 11 is arranged at the front of the tapes, the magnifying lenses of the microscope 11 face the surface of the film carrier tapes T1 and T2 to be inspected along the horizontal direction. That is, the focal length of the lenses is along the horizontal direction. Accordingly, the distance L from the eyepiece P1 to the inspection position P2 of the film carrier tapes T does not change in a vertical direction when the magnification is adjusted, as shown in FIG. 7. The height of the microscope 11 is freely adjustable by sliding mechanism depending on the inspector's sitting height.

In the conventional inspection apparatus as described above, the magnification adjustment is accompanied with upward or downward movement of the eyepiece by the change of the distance L. On the other hand, the constitution of the present embodiment ensures a required magnification without vertical movement of the eyepiece.

Figure 9:
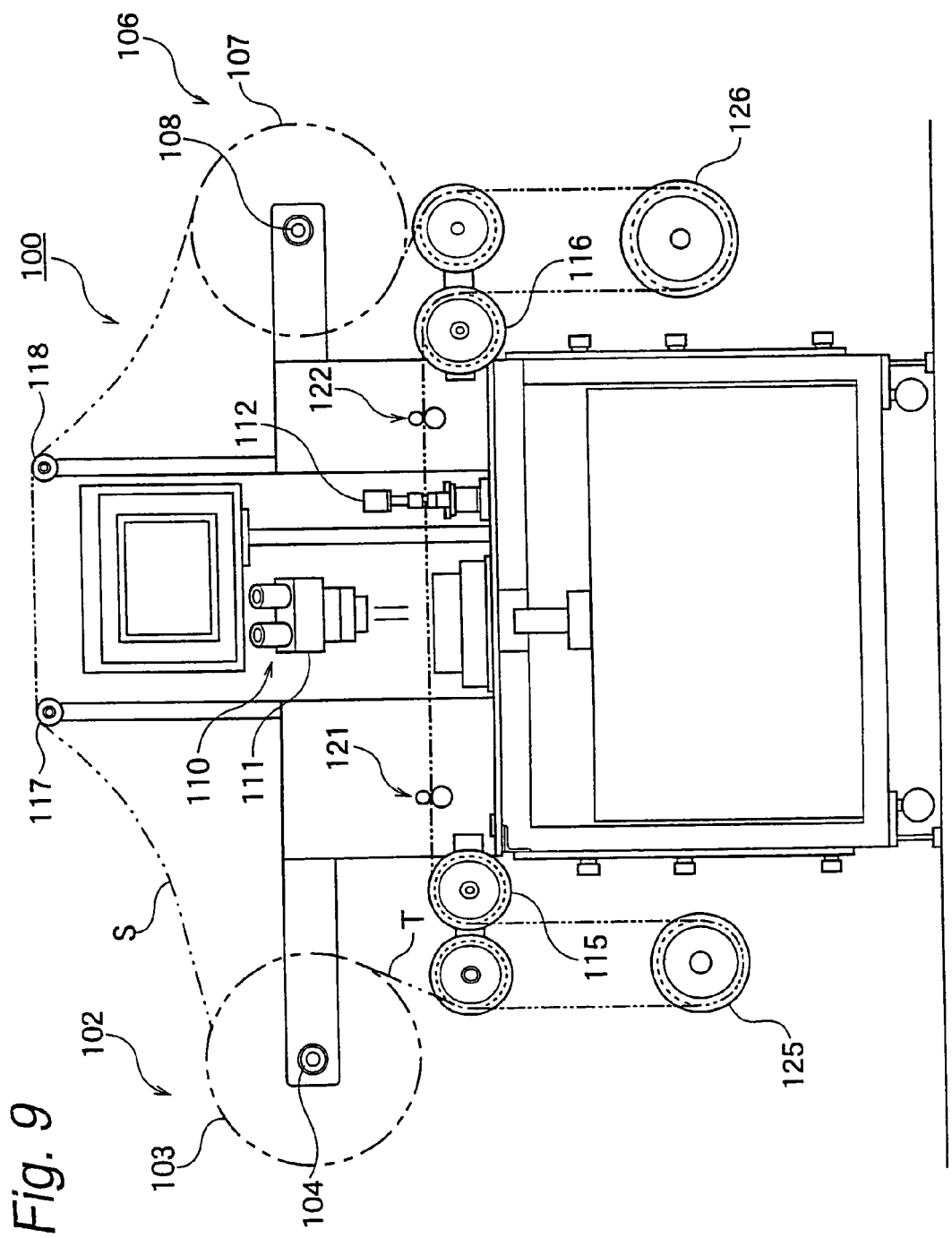
FIG. 9 is a front view illustrating a conventional inspection apparatus for film carrier tapes.
Figure 6:
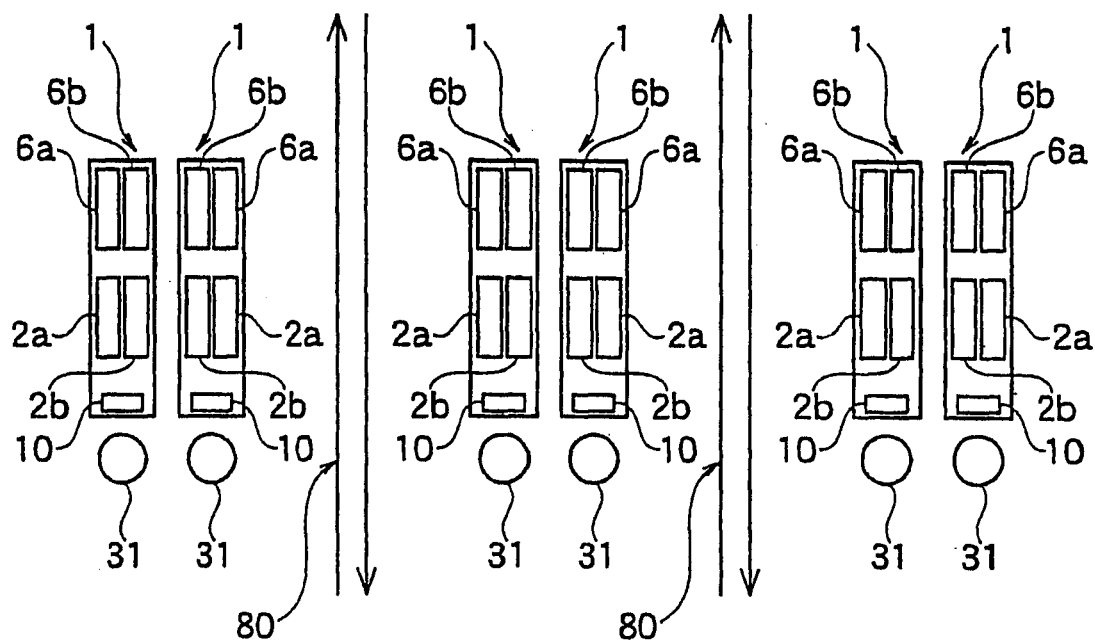
Figure 6:
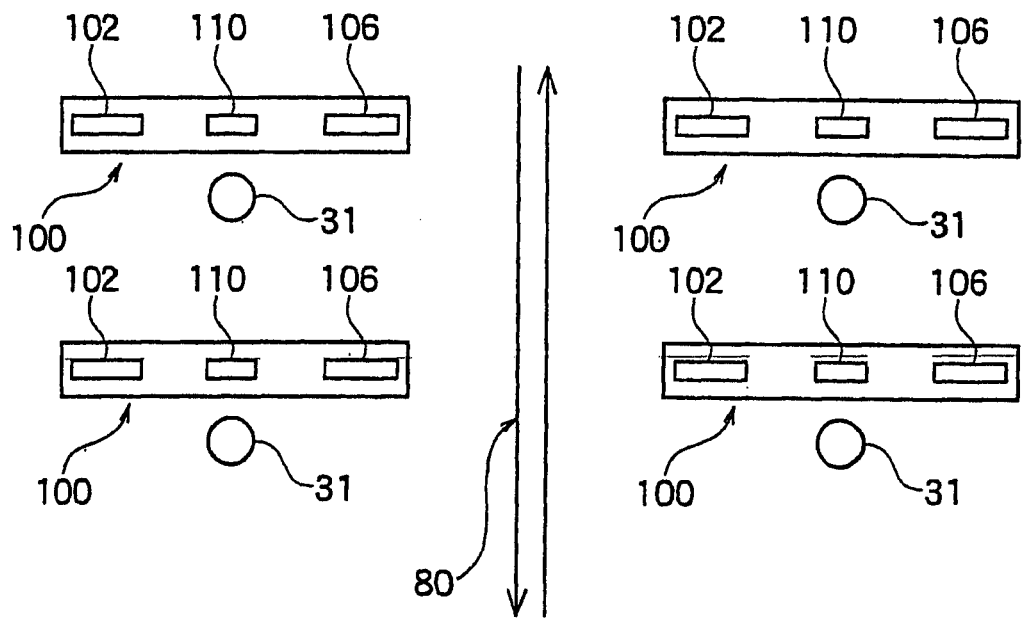

When the inspector sitting on a chair of ordinary height conducts inspection using the conventional inspection apparatus as illustrated in FIG. 9, the magnification of the magnifier will be generally less than 2×. At a less than 2× magnification, visual inspection for defects is possible for the pitches between the wiring patterns of 75 µm at best, and generally 100 µm or more. Meanwhile, the constitution of the present embodiment in which the film carrier tapes are inspected along a vertical direction enables the seated inspector to conduct visual inspection of the wiring patterns with pitches of 75 µm or less, and ultimately down to 50 µm.

Figure 2:
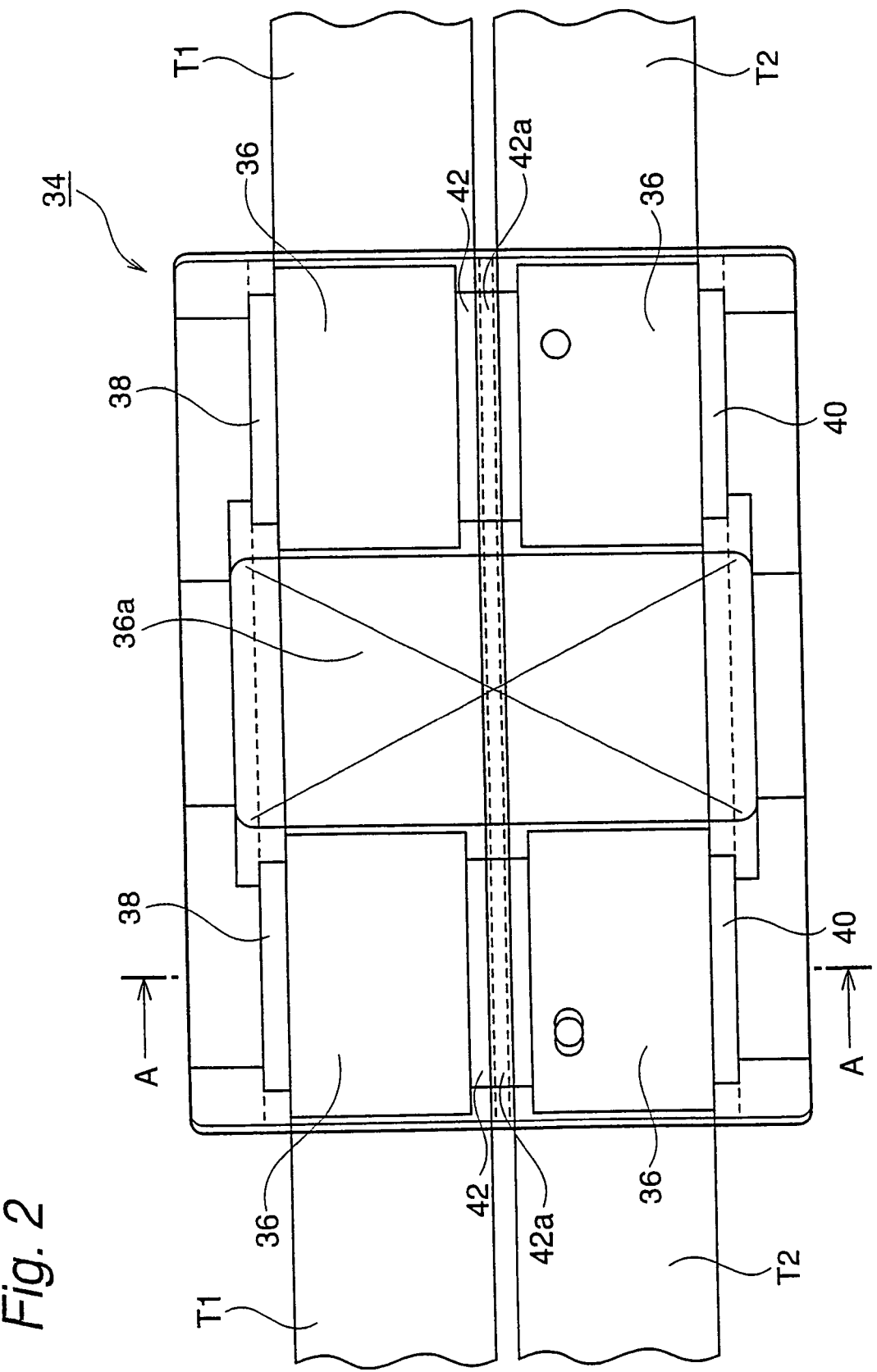
FIG. 2 is a front view of a guide member of an inspection part.
Figure 3:
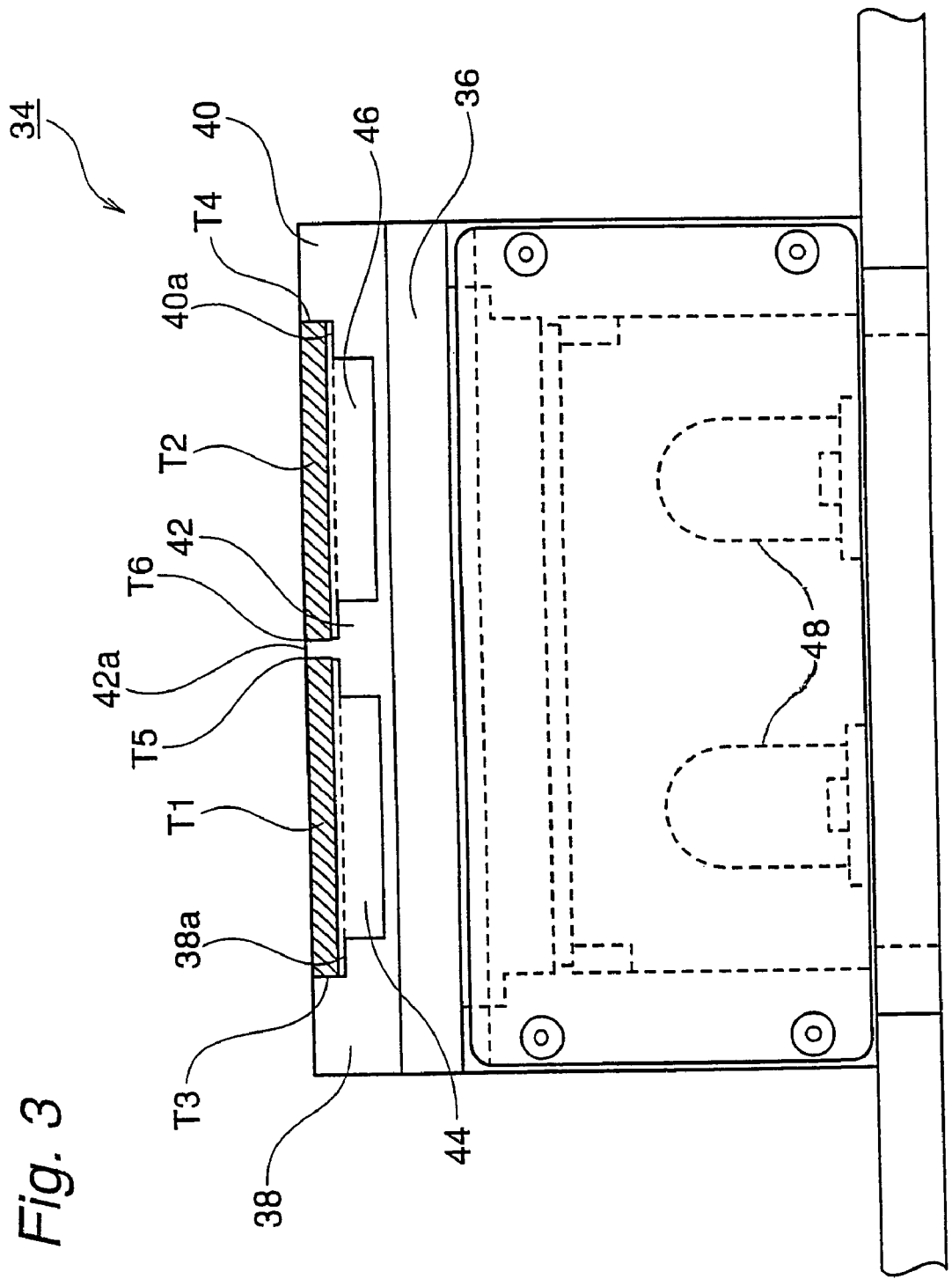
FIG. 3 is a sectional view along the A-A line in FIG. 2.

FIGS. 2 and 3 show an example of transportation configuration of the film carrier tapes T1 and T2 at the inspection part 10. When the visual inspection is performed at the inspection part 10, the transportation by driving the drive gear illustrated in FIG. 1 is temporarily stopped so that the pieces G to be inspected will be located at a predetermined position of a guide member 34. For example, when the visual inspection is performed by transmitted light, the pieces G are located at a window 36*a* through which light from an irradiation device 48 passes.

The guide member 34 is approximately U-shaped in cross section as illustrated in FIG. 3. It has side guide members 38 and 40 protrudent from both ends of substrates 36 at the back, toward the front (toward the microscope 11). The side guide members 38 and 40 guide both outermost edges T3 and T4 of the film carrier tapes T1 and T2.

The side guide members 38 and 40 are formed with respective steps 38*a* and 40*a* along which both the outermost edges T3 and T4 of the film carrier tapes T1 and T2 are guided.

Between the side guide members 38 and 40 at both ends are provided an adjacent parts guide member 42 having a flat forward surface protrudent from the substrate 36 so as to guide adjacent sides T5 and T6 of the film carrier tapes T1 and T2.

The adjacent parts guide member 42 is formed with a separation protrusion 42*a* that divides the flat forward surface which guides the film carrier tapes T1 and T2, so as to prevent abrasive wear of the adjacent sides T5 and T6 by contacting each other. The width of the separation protrusion 42*a* is not particularly limited, but is suitably about 3 mm to ensure separation of the sides T5 and T6.

Between the side guide members 38 and 40 each and the adjacent parts guide member 42, spaces 44 and 46 are provided to prevent frictional damage or the like to the bottom surface of the film carrier tapes T1 and T2 during transportation.

According to the transportation configuration of the film carrier tapes T1 and T2 at the inspection part 10 described above, the outermost edges T3 and T4 and the adjacent sides T5 and T6 are all supported by the side guide members 38 and 40 and the adjacent parts guide member 42 of the guide member 34 during the transportation of the film carrier tapes T1 and T2. Accordingly, the film carrier tapes T1 and T2 being transported in parallel to each other at the inspection part 10 will not be bent (distorted) in the width direction during transportation. Therefore, the tapes may be prevented from being misaligned from the focal position of the magnifier at the inspection position. Thus, the wiring patterns may be visually observed with accuracy to allow reliable quality inspection. It is also possible that pressing rollers are provided at the upstream and downstream of the guide member 34 and the guide member 34 is inclined 1 to 45° away from the inspector.

After the inspection, the film carrier tapes T1 and T2 are guided by the lower guide roller 29 of FIG. 1 such that the direction of the tapes is turned from the substantially vertical direction to a substantially horizontal direction toward the take-up reels 7a and 7b. The horizontal direction may be inclined upward or downward depending on the layout of the apparatus.

On the transportation route along the horizontal direction, a defect marking device 12 is located that marks a defect mark on the film carrier tapes T1 and T2 by punching or ink marking. A piece G found to be rejected by the visual inspection at the inspection part 10 is marked as such on a predetermined position thereof by the defect marking device 12. It is also possible that the defect marking device 12 is located at a vertical point upstream of the lower guide roller 29, between the inspection part 10 and the lower guide roller 29.

The film carrier tapes T1 and T2 guided by the guide rollers 28, 29 and 16 define a reversed L-like shape as shown in FIG. 1. The L-shaped film carrier tapes T1 and T2 undergo tension in opposite directions by an upstream dancer roller 25 and a downstream dancer roller 26. The film carrier tapes T1 and T2 under tension are transported by driving the drive gear 22 provided at the downstream of the lower guide roller 29, on the transportation route along the substantially horizontal direction.

Figure 4:
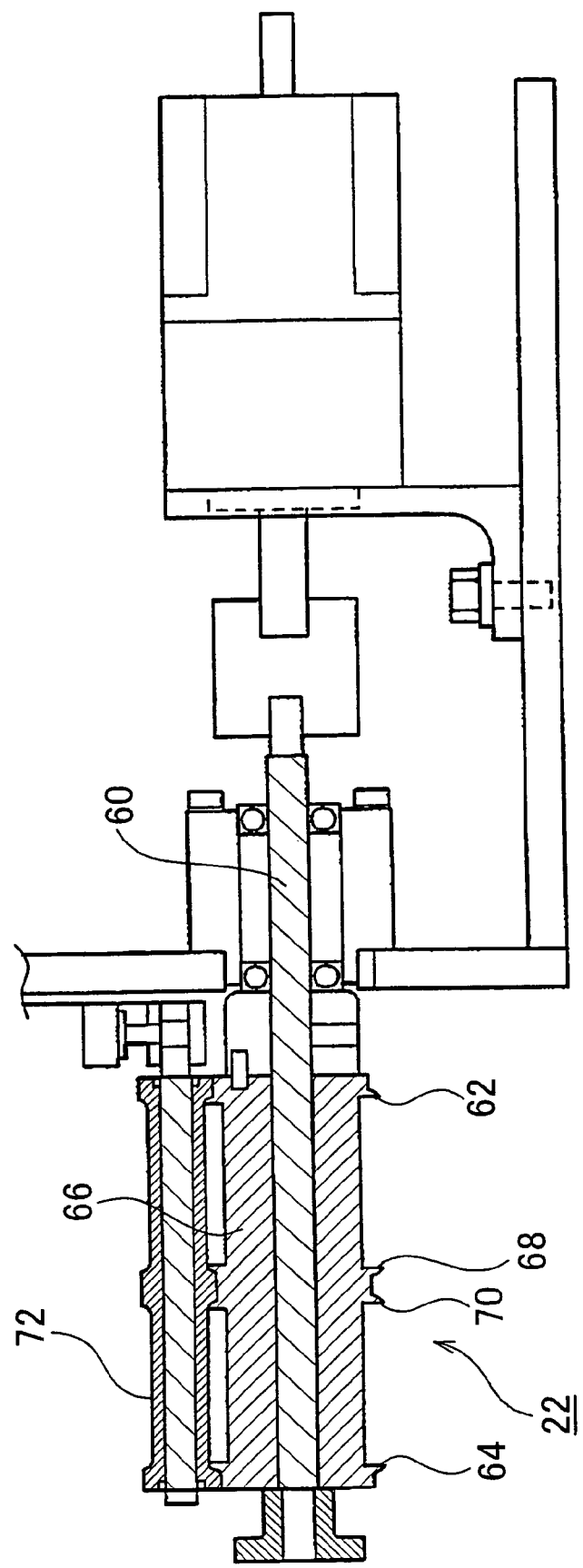
FIG. 4 is a schematic view of a drive gear of the inspection apparatus shown in FIG. 1.

The drive gear 22 includes, as shown in FIG. 4, a shaft 60, a roller body 66 fitted to the shaft 60, distal gears 62 and 64 at both ends of the roller body 66, and intermediate gears 68 and 70 at a central area of the roller body 66. The roller body 66 is made of a synthetic resin such as PTFE (polytetrafluoroethylene) or fluororesin.

The distal gears 62 and 64 engage with sprocket holes H3 and H4 bored in the outermost edges T3 and T4 of the film carrier tapes T1 and T2 as illustrated in FIG. 5.

The intermediate gears 68 and 70 engage with sprocket holes H5 and H6 bored in the adjacent sides T5 and T6 of the film carrier tapes T1 and T2.

To ensure stable transportation, a pressing roller 72 is provided so that the film carrier tapes T1 and T2 are interposed between the pressing roller 72 and the drive gear 22.

A drive motor rotates the shaft 60 together with the roller body 66, and thereby the distal gears 62 and 64 and the intermediate gears 68 and 70 of the drive gear 22 are engaged with the sprocket holes H3 to H6 bored in the outermost edges T3 and T4 and the adjacent sides T5 and T6. Thus, the film carrier tapes T1 and T2 are transported in parallel at the same speed.

Accordingly, the film carrier tapes T1 and T2 can be transported in parallel to each other without misalignment and be inspected at the inspection part 10 simultaneously and with accuracy. The drive gear 22 may be replaced with a drive roller without gears for protection of the sprocket holes.

After the visual inspection and the defect marking, the film carrier tapes T1 and T2 are guided by the guide roller 16 and a guide roller 30, and the film carrier tape T1 is wound on the take-up reel 7a and the film carrier tape T2 on the take-up reel 7b.

Specifically, a drive motor (not shown) drives to rotate the take-up drive shaft 8a and the film carrier tape T1 is wound on the take-up reel 7a together with the spacer S1. Meanwhile, a drive motor (not shown) drives to rotate the take-up drive shaft 8b and the film carrier tape T2 is wound on the take-up reel 7b, with the spacer S2 interposing between the layers of tape wound on the take-up reel 7b.

The inspection apparatus 1 of the present embodiment described hereinabove has the following constitution. The feed reels and the take-up reels are arranged adjacent to each other in a substantially horizontal direction along the reel diameter, and the inspection part is located on the opposite side of the feed reels to the take-up reels. The film carrier tapes for mounting electronic components are fed from the feed reels toward the inspection part, and are transported in the substantially vertical direction at the inspection part. Thereafter, the film carrier tapes below the feed reels are transported and wound on the take-up reels.

The above constitution achieves reduction approximately by half of the area for placement of the apparatus as compared to the conventional constitution in which the inspection part is located between the feed reel and the take-up reel and the film carrier tape is transported in a horizontal direction across the inspection part.

Because of the adjacent arrangement of the feed reels and the take-up reels, the spacers can be transported from the feed reels directly to the take-up reels. Thus, the present embodiment permits elimination of the spacer guide rollers 117 and 118 of the conventional inspection apparatus 100 illustrated in FIG. 9.

In the prior art as shown in FIG. 6(B), the inspection part 110 is located at the center in the longer direction of the inspection apparatus 100 and the inspector 31 faces the inspection part 110 from a direction that is perpendicular to the longer direction of the inspection apparatus 100. Therefore, the inspection apparatuses 100 need to be arranged in a room as illustrated in the figure, and the space between the edges in the width direction of the apparatuses 100 and 100 is used as passageways 80.

On the other hand, the inspection apparatus 1 of the present embodiment is constituted, as shown in FIG. 6(A), such that the inspection part 10 is located at an end in the width direction of the inspection apparatus 1 and the inspector 31 faces the inspection part 10 from a direction perpendicular to the width direction of the inspection apparatus. Accordingly, when a pair of the inspection apparatuses 1 and 1 having a mirror-image relation (as right and left hands) are arranged with their back faces opposed to each other, both sides in the width direction of a pair of the inspection apparatuses 1 and 1 can be used as passageways 80 as illustrated. Therefore, the space inside the inspection room can be more effectively used as compared with the conventional inspection apparatuses 100.

With the traditional apparatus as shown in FIG. 9, the inspector conducts visual inspection of the film carrier tape that is transported in a lateral direction across his field of view. Following the movement of the film carrier tape by eyes can cause the inspector to feel sick during the inspection, similar to seasickness. In contrast, the apparatus of the present embodiment allows the inspector to inspect the film carrier tapes that are transported in a vertical direction across his field of view. Accordingly, it is very unlikely that the inspector feels sick during the visual inspection.

Although the inspection apparatus for film carrier tapes according to the present invention has been described by the embodiment in which two film carrier tapes (T1 and T2) are simultaneously inspected. However, the inspection apparatus of the present invention is not limited to the embodiment and can be constituted to inspect one film carrier tape or three or more film carrier tapes.

In the above embodiment, the tapes are transported from above to below the inspection part 10, namely, from the upper guide roller 28 to the lower guide roller 29. However, it is possible that the transportation direction is reversed, that is, the tapes may be transported from the lower guide roller 29 to the upper guide roller 28.

Further, in the above embodiment, the film carrier tapes are transported from the upper guide roller to the lower guide roller, and are transported toward the take-up reels via below the feed reels. However, it is possible that a guide roller is arranged at an appropriate position and the film carrier tapes are transported from the lower guide roller to the upper guide roller and further transported toward the take-up reels via above the feed reels.

Preferably, the tapes at the inspection part 10 are vertical, but the inspection can be performed without problems even if the tapes are transported toward the inspector at an angle of, for example, 1 to 45°.

Although the defect marking device in the above embodiment is located at the downstream of the inspection part along the horizontal direction, it may be located at an arbitrary position downstream of the inspection part, for example on the inclined or vertical transportation route to the take-up reels.

In the above embodiment, the feed reels and the take-up reels adjacent to each other are arranged in the order of the feed reels and the take-up reels from the inspection part. But this order may be reversed where necessary.

Although in the above embodiment the inspection is conducted visually by the inspector at the inspection part, automatic quality inspection using a computer is also possible in which the computer performs image recognition by analyzing an image data taken in a CCD camera. Also, the inspection may be made visually based on a CCD camera image.

The inspection apparatus and method according to the present invention can be applied to the visual inspection of packages with electronic components (semiconductor devices).

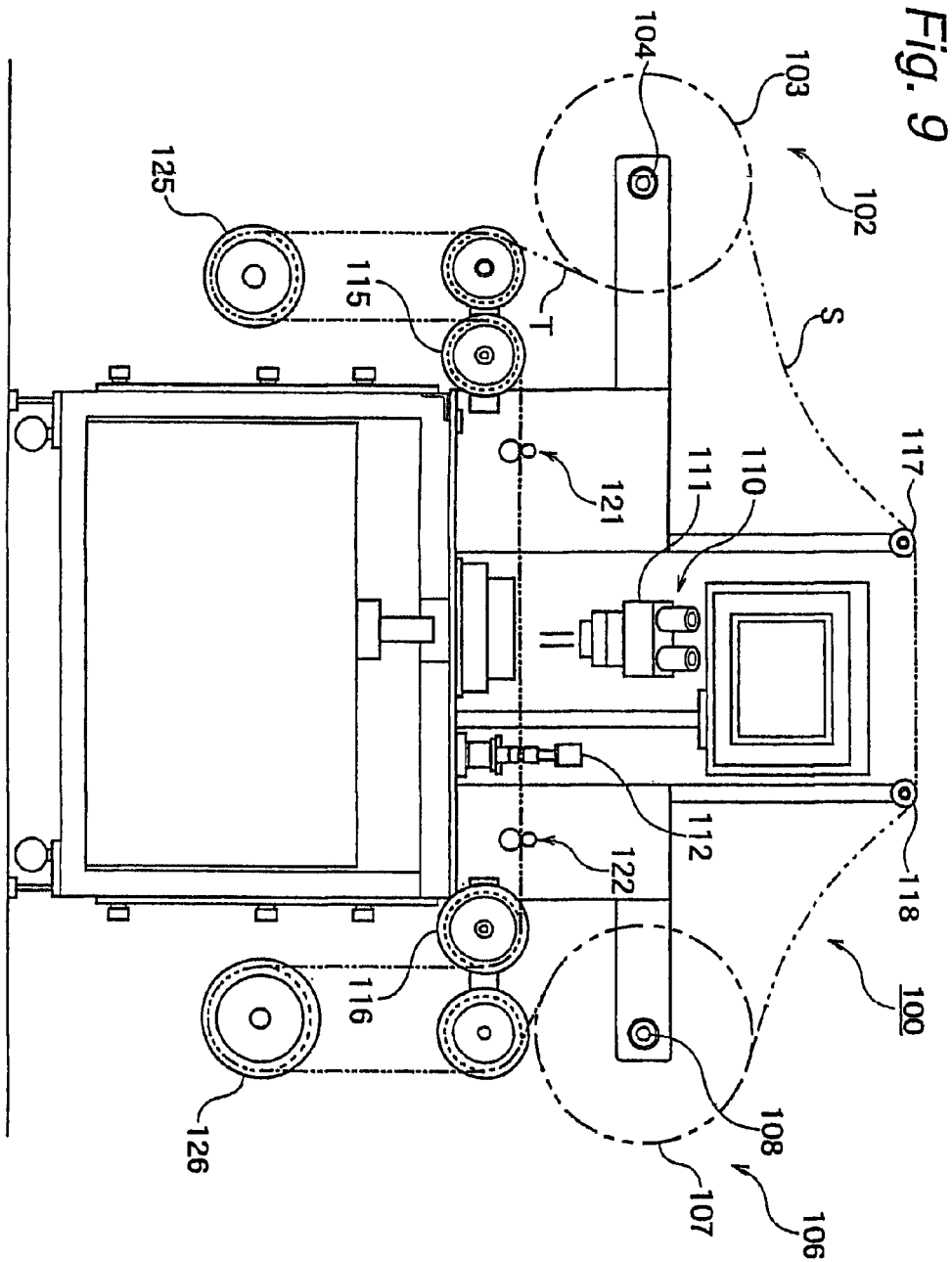

What is claimed is:

1. An inspection apparatus for film carrier tapes for mounting electronic components, comprising:
    a feed device for feeding a film carrier tape wound on a feed reel;
    an inspection part for inspecting the film carrier tape; and
    a take-up device for winding up the film carrier tape inspected at the inspection part on a take-up reel;
    wherein the feed reel and the take-up reel are arranged adjacent to each other, and the inspection part is located so that the adjacent feed and take-up reels are in the order of the feed reel and the take-up reel or the take-up reel and the feed reel in relation to the inspection part, thereby a spacer is transported from the feed reel to the take-up reel directly, not via a spacer guide roller, and the film carrier tape is transported in a substantially vertical direction at the inspection part so that the film carrier tape along the substantially vertical direction is inspected with a magnifier.

2. The inspection apparatus according to claim 1, further comprising an upper guide roller and a lower guide roller above and below the inspection part respectively to transport the film carrier tape in a substantially vertical direction from the upper guide roller to the lower guide roller or from the lower guide roller to the upper guide roller.

3. The inspection apparatus according to claim 2, characterized in that the lower guide roller guides the film carrier tape such that the traveling direction of the tape is turned from the substantially vertical direction extending from the upper guide roller to the lower guide roller, to a substantially horizontal direction toward the side of the take-up reel, wherein the inspection apparatus further comprises a drive gear that is driven to transport the film carrier tape, the drive gear being provided at a position along the substantially horizontal direction, and tension devices at the upstream of the upper guide roller along the transportation direction and at the downstream of the drive gear along the transportation direction.

4. The inspection apparatus according to claim 3, further comprising a defect marking device at a position along the substantially horizontal direction for marking a defect mark on the film carrier tape.

5. The inspection apparatus according to claim 1, comprising a plurality of pairs of the feed reel and the take-up reel adjacent to each other, wherein a plurality of the film carrier tapes fed from the respective feed reels are transported in parallel with each other in a substantially vertical direction at the inspection part and the film carrier tapes along the substantially vertical direction are inspected with a magnifier.

6. The inspection apparatus according to claim 1, characterized in that the apparatus allows an inspector to conduct visual inspection of the film carrier tape at the inspection part in which the film carrier tape is transported in a vertical direction across the field of view of the inspector.

7. The inspection apparatus according to claim 1, which is for inspecting semiconductor devices instead of the film carrier tape, the semiconductor devices including a film carrier tape and electronic components mounted thereon.

8. The inspection apparatus according to claim 7, characterized in that it allows an inspector to conduct visual inspection of the semiconductor devices at the inspection part in which the semiconductor devices are transported in a vertical direction across the field of view of the inspector.

9. An inspection method for film carrier tapes for mounting electronic components, which method comprising transporting a film carrier tape fed from a feed reel in a substantially vertical direction at an inspection part, and inspecting the film carrier tape along the substantially vertical direction with a magnifier and transporting a spacer from the feed reel directly to the take-up reel, not via a spacer guide roller,
    wherein the inspection part is located so that the adjacent feed and take-up reels are in the order of the feed reel and the take-up reel or the take-up reel and the feed reel in relation to the inspection part.

10. The inspection method according to claim 9, wherein the feed reel and the take-up reel are arranged adjacent to each other.

11. The inspection method according to claim 9, further comprising transporting the film carrier tape in a substantially vertical direction from an upper guide roller to a lower guide roller or from a lower guide roller to an upper guide roller, the upper guide roller and the lower guide roller being provided above and below the inspection part respectively.

12. The inspection method according to claim 11, further comprising:
    guiding the film carrier tape by the lower guide roller such that the traveling direction of the tape is turned from the substantially vertical direction extending from the upper guide roller to the lower guide roller, to a substantially horizontal direction toward the side of the take-up reel;

transporting the film carrier tape by driving a drive gear provided at a position along the substantially horizontal direction; and applying tension by tension devices to the film carrier tape that is folded by the lower guide roller from the substantially vertical direction to the substantially horizontal direction, the tension devices being arranged at the upstream of the upper guide roller along the transportation direction and at the downstream of the drive gear along the transportation direction.

13. The inspection method according to claim 12, further comprising marking a defect mark on the film carrier tape by a defect marking device provided at a position along the substantially horizontal direction.

14. The inspection method according to claim 9, comprising:

feeding a plurality of the film carrier tapes from a plurality of the feed reels paired with a plurality of the take-up reels, the feed reels and the take-up reels being adjacent to each other;

transporting the film carrier tapes in parallel with each other in a substantially vertical direction to the inspection part; and inspecting the film carrier tapes parallel to each other along the substantially vertical direction with a magnifier.

15. The inspection method according to claim 9, wherein an inspector conducts visual inspection of the film carrier tape that is transported at the inspection part in a vertical direction across the field of view of the inspector.

16. The inspection method according to claim 9, wherein semiconductor devices are inspected instead of the film carrier tape, the semiconductor devices including a film carrier tape and electronic components mounted thereon.

17. The inspection method according to claim 16, wherein an inspector conducts visual inspection of the semiconductor devices that are transported at the inspection part in a vertical direction across the field of view of the inspector.

* * * * *

UNITED STATES PATENT AND TRADEMARK OFFICE
CERTIFICATE OF CORRECTION

PATENT NO. : 7,500,502 B2 Page 1 of 3
APPLICATION NO. : 11/058858
DATED : March 10, 2009
INVENTOR(S) : Yamamoto et al.

Figure 6:
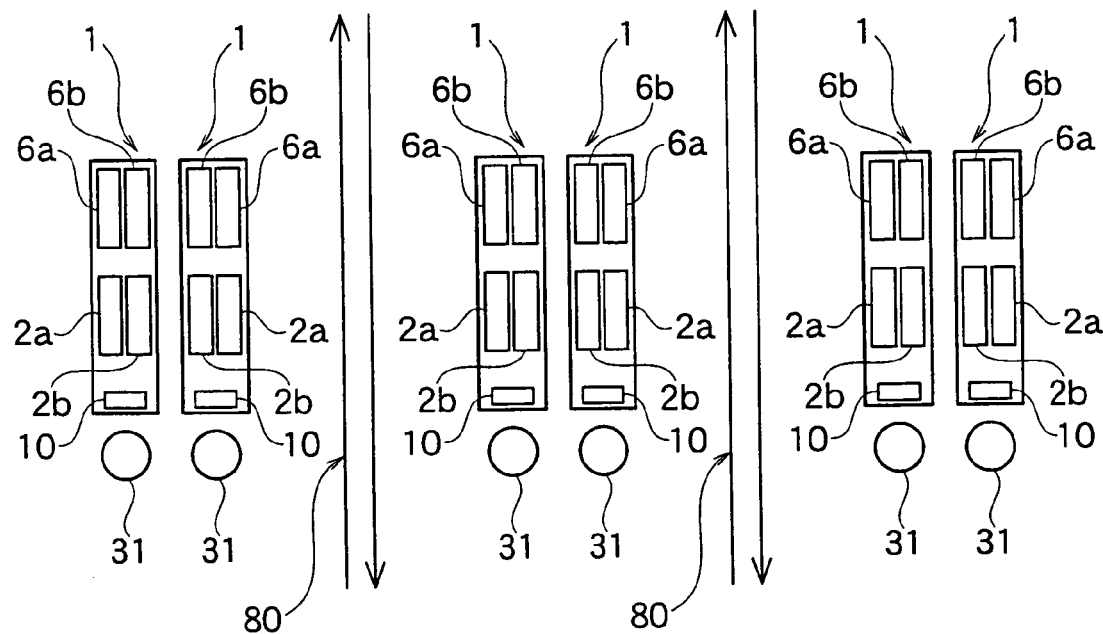
FIG. 6(A) is a plan view illustrating an indoor arrangement of the inspection apparatuses according to the present invention and FIG. 6(B) is a plan view showing an indoor arrangement of the conventional inspection apparatuses.
Figure 6:
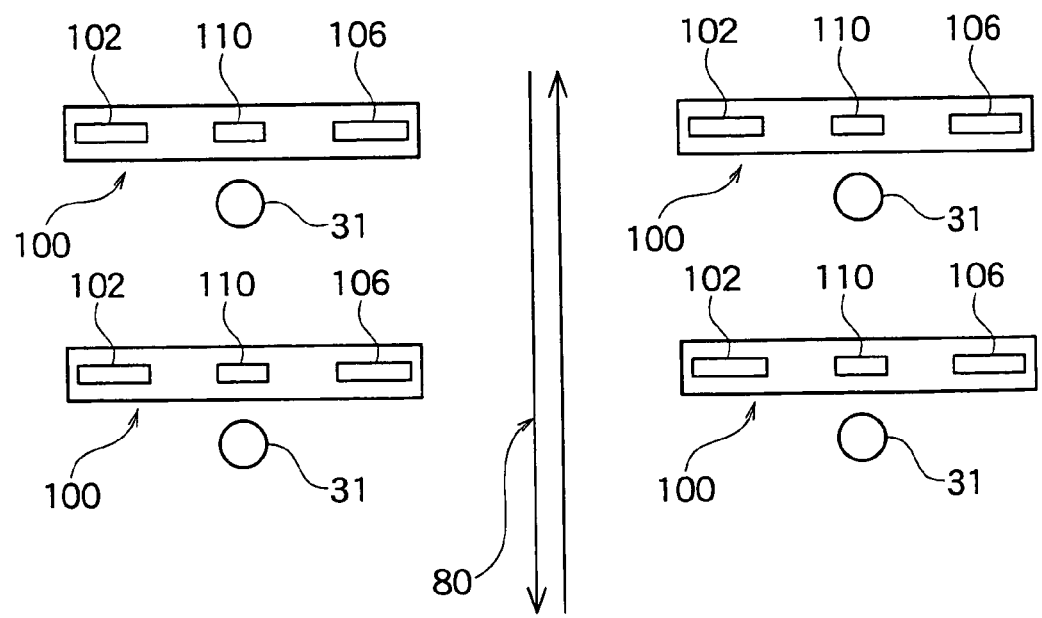

It is certified that error appears in the above-identified patent and that said Letters Patent is hereby corrected as shown below:

Substitute the printed drawing FIG. 6 (B) and drawing FIG. 9 with the attached replacement drawing FIG. 6 (B) (PRIOR ART) and drawing FIG. 9 (PRIOR ART).

Signed and Sealed this

Sixteenth Day of March, 2010

David J. Kappos
*Director of the United States Patent and Trademark Office*

(A)

(B) Prior Art